United States Patent [19]

Konig

[11] 4,068,529
[45] Jan. 17, 1978

[54] METHOD AND APPARATUS FOR AUTOMATICALLY PERFORMING SERIES ANALYSES

[75] Inventor: Eberhard Konig, Uberlingen, Germany

[73] Assignee: Bodenseewerk Perkin-Elmer & Co. GmbH, Uberlingen, Bodensee, Germany

[21] Appl. No.: 760,568

[22] Filed: Jan. 19, 1977

[30] Foreign Application Priority Data

Jan. 24, 1976 Germany .............................. 2202675

[51] Int. Cl.$^2$ ............................................. G01N 1/12
[52] U.S. Cl. .................................... 73/423 A; 73/1 R
[58] Field of Search ............... 73/1 R, 423 A; 23/230, 23/259

[56] References Cited

U.S. PATENT DOCUMENTS

| | | | |
|---|---|---|---|
| 3,192,968 | 7/1965 | Baruch | 73/423 A |
| 3,508,442 | 4/1970 | Lightner | 73/423 A |
| 3,529,475 | 9/1970 | Lightner | 73/423 A |
| 3,581,574 | 6/1971 | Smith | 73/423 A |
| 3,666,420 | 5/1972 | Paatzsch | 73/423 A |
| 3,800,984 | 4/1974 | Phelan | 23/253 |
| 3,902,371 | 9/1975 | Hooper | 73/423 A |

*Primary Examiner*—S. Clement Swisher
*Attorney, Agent, or Firm*—S. A. Giarratana; F. L. Masselle; E. T. Grimes

[57] ABSTRACT

Automatic sample preparation method and apparatus for making successive measurements with an analyzer by picking up with a single stepwise movable metering probe, in a first measuring cycle, a sample for measurement from a sample container and a small volume of air; introducing this sample and the air into the inlet of the analyzer; picking up with the same metering probe, in a secondary measuring cycle, a sample for measurement from the same sample container and a small volume of air, and picking up with said metering probe a metered quantity of liquid additive and a second small volume of air; and thence introducing said sample, said liquid additive and said air picked up in the secondary measuring cycle into the inlet of the analyzer.

23 Claims, 8 Drawing Figures

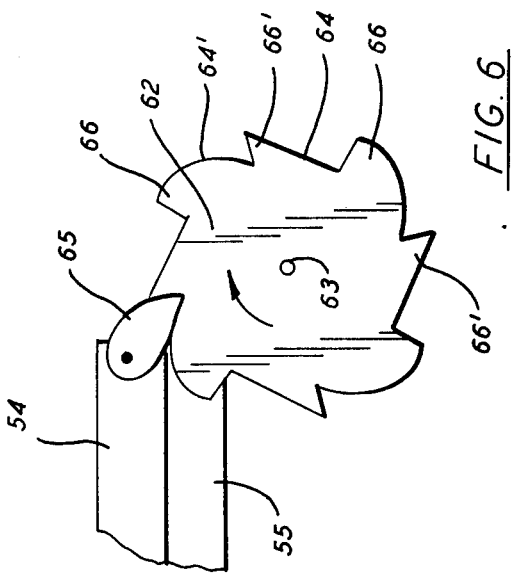
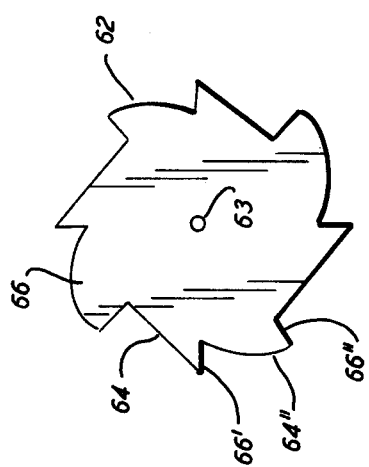
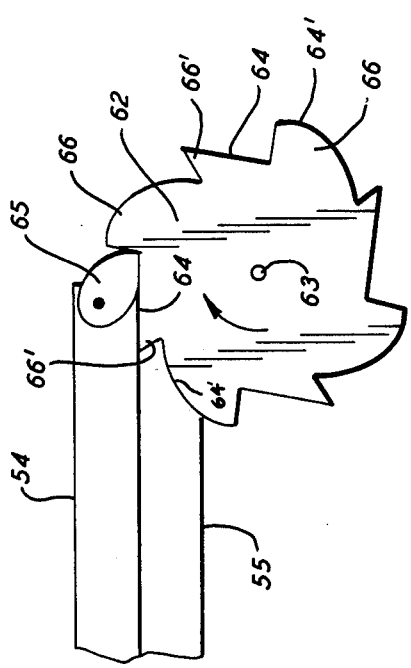

4,068,529

METHOD AND APPARATUS FOR AUTOMATICALLY PERFORMING SERIES ANALYSES

BACKGROUND OF THE INVENTION

1. Field of the Invention

This invention relates to sampling method and apparatus for analytical equipment and, in particular, to such method and apparatus that is adapted for automatically performimg series analyses.

2. Description of the Prior Art

In U.S. patent application Ser. No. 660,194 filed on Feb. 20, 1976 and assigned to the Assignee of the present application, there is disclosed apparatus wherein samples to be measured are taken up from successive sample containers and sequentially supplied to an atomic absorption spectrometer. Means are provided to prevent errors in the measured results due to carry-over of the sample material or other contaminations. The automatically controlled sequence of the individual operating steps permits series analyses to be performed, whereby the measured signals may be evaluated in a data processor.

It will be appreciated that such a method of analysis, however, will not always yield reliable measuring results, particularly if the signals obtained depend on detector sensitivity or sample composition. Thus, for instance, the indicator sensitivity of thermionic detectors in gas chromatography which respond selectively to halogen, phosphorus or nitrogen containing compounds are dependent on ageing effects. In sample liquids like blood, substances which are inherently present may affect the signal measured so that a calibration curve obtained for one liquid sample may not be applicable to the same sample of different origin. In such cases it is, therefore, necessary to conduct separate reference measurements for each individual sample.

In methods of measurement responsive to the quantity of the component to be determined in the sample, i.e., gas chromatography and atomic absorption spectroscopy, the procedure is to perform at least one additional measurement with the same sample, with a known amount of the component to be determined being added to the sample. Said known amount is added as a metered quantity of a liquid additive containing the desired component dissolved in a solvent. Additionally, a corresponding quantity of the pure solvent is added to the sample being measured, per se, before taking its measurement. The respective dilution is then taken into consideration in the subsequent evaluation of the measured signals. See, for example, the publication entitled, "Analysentechnische Berichte", Vol. 32, (1974) page 10.

SUMMARY OF THE INVENTION

The basic and general object of the present invention is the provision of sampling methods and apparatus which are improvements over the known prior art systems.

An object to be achieved by the invention resides in the provision of an automatic operating method of analysis and analysis apparatus wherein, independent of the method of measurement employed, in addition to the actual sample measurement, one or more reference measurements are made to thereby render the results obtained with the analysis apparatus independent of the composition of the sample liquid and variations in the apparatus response characteristics.

To the accomplishment of the foregoing objectives, and additional object and advantages, which will become apparent as this description proceeds, the invention contemplates in one form thereof the provision of a new and improved method for making successive measurements with an analyzer comprising, for each complete cycle of operation, in controlled sequence, the steps of: picking up with a single stepwise movable probe, in a first measuring cycle, a sample for measurement from a sample container and a small volume of air. The next steps in the method comprise: introducing said sample and the small volume of air into the inlet of the analyzer; picking up with the same metering probe, in a secondary measuring cycle, a sample for measurement from the same sample container and a small volume of air, and then picking up with the metering probe a metered quantity of liquid additive and a second small volume of air; and thereafter introducing said sample, said liquid additive and said air picked up in the secondary measuring cycle into the inlet of the analyzer.

According to one aspect of the invention, there are a plurality of secondary measuring cycles in which different, respective, liquid additives are picked up by the metering probe and introduced into the inlet of the analyzer, and according to another aspect preselected amounts of the same liquid additive are picked up in the secondary measuring cycles, respectively.

Further, according to another aspect of the invention, the liquid additive in each secondary measuring cycle contains a predetermined concentration of a solvent of the component to be determined in the sample.

In the simplest case, wherein the dilution by the liquid additive does not affect the signal measured, there is obtained one, or a number of signals from measurements in which a predetermined, known quantity of the desired component has been added. At least one reference measurement is therefore obtained for each measurement taken of a sample In cases in which the addition of the liquid additive affects the measured signal, a quantity of solvent may be taken up in the first measuring cycle, which is equal to the added quantity of liquid additive in the secondary measuring cycles. Also, with different amounts of liquid additive added in the secondary measuring cycles, different quantities of solvent may be taken up, corresponding to the respective quantities of liquid additive in each of the secondary cycles.

In both of the cases just discussed, it is immaterial whether or not the measurements of the samples, with or without the added solvent, are taken prior to or after the measurement with the liquid additive. Equal quantities of the liquid additives containing different amounts of the desired components in the same solvent may be employed and also, different quantities of the same liquid additive containing a predetermined amount of the desired component in a solvent may be added. Nevertheless, the measured results may be corrected in a known manner in such a way as to be comparable.

In one form thereof, the invention provides new and improved automatic sample preparation apparatus for making successive measurements with an analyzer which comprises, in combination, a base plate; a rotatable table for receiving a plurality of sample containers mounted for rotation on the base plate, and means for controlling the advance of the table in a stepwise manner in accordance with the number of measuring cycles in a complete cycle of operation. In addition, the apparatus of the invention includes a rinse fluid container mounted on the base plate; a liquid additive container mounted on the base plate adjacent the rinse fluid container; and means mounting the base plate for pivotal movement between a fixed stop and a variable stop means, respectively. A metering probe is provided which has a capillary tip, and means are provided for mounting the probe for pivotal movement about two mutually normal axes to dip the tip into said containers one at a time and into the inlet of the analyzer. Pumping means, including a stepping motor, serve to pass rinse fluid through the metering probe to the rinse container and for picking up metered quantities of liquid in said capillary tip from the sample containers and from the liquid additive container for delivery to the inlet of the analyzer. A central control unit serves to coordinate the movement of the base plate, rotatable table, metering probe and pumping means.

It will be appreciated that by means of the apparatus according to the invention, the base plate may be pivoted in such a way underneath the metering probe that a sample for measurement can be taken up, that the metering probe can then be rinsed or washed externally, that subsequently liquid additive can be taken up, and that finally after further external rinsing the liquid so picked up is delivered to the inlet of the analyzer. In addition, a small volume of air is taken up into the metering probe between each respective pick up of liquid and liquid additive. The variable stop means for the base plate enables the pivoting thereof to be controlled in accordance with a predetermined program. The employment of stepping motors in the pumping system has the advantage that the pick up and delivery of liquid into and from the metering probe can be very precisely controlled.

The time sequence of the steps in the method may be controlled by the central control unit. Also, the number of steps of the stepping motors may be adjusted by this unit. A data processor may be provided for evaluation of the signals measured, which is in communication with the central control unit. The data processor may consitute a microcomputer built into the apparatus, and the time-programmed control as well as the number of steps employed in the pump stepping motors may be stored therein. This system optimally controls the cooperation of the members of the apparatus according to the invention, as well as the sequence of the individual operational steps.

According to one aspect of the invention, the variable stop means includes a rotatable ratchet wheel having a plurality of alternately disposed teeth and stop faces, and a pawl linked to the base plate for coacting with the ratchet wheel in operative relationship, the number of stop faces on the ratchet wheel being equal to the number of pivoting movements of the base plate in one measuring cycle.

According to another aspect of the invention, the means for controlling the advance of the rotatable table includes a cam rotatable with the ratchet wheel of the variable stop means, a stop latch engageable with serrations on the rotatable table, and linking means coupling the cam and the stop latch to thereby control the advance of the rotatable table in accordance with the number of measuring cycles in a complete cycle of operation.

Advantageously, the metering probe according to the invention is externally rinsed prior to the take-up of liquid additive and prior to the delivery to the inlet of the analyzer. Further, according to an aspect of the invention, the metering probe is rinsed internally and externally between each complete cycle of operation.

It is within the concept of the invention, with respect to both the method and apparatus, that each of the samples to be measured may be taken up by the metering probe and initially delivered to an intermediate vessel, from which it may then be supplied one or more times to the inlet of the analyzer.

There has been thus outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended hereto. Those skilled in the art will appreciate that the conception upon which the disclosure is based may readily be utilized as a basis for the designing of other method and apparatus for carrying out the several purposes of the invention. It is important, therefore, that the claims be regarded as including such equivalent method and apparatus as do not depart from the spirit and scope of the invention.

Specific embodiments of the invention have been chosen for purposes of illustration and description, and are shown in the accompanying drawings, forming a part of the specification.

BRIEF DESCRIPTION OF THE DRAWINGS

FIG. 5 is an enlarged plan view of the variable stop means for the base plate in one operational position;

FIG. 6 is an enlarged plan view similar to FIG. 5, but showing another operational position;

FIG. 7 is an enlarged plan view similar to FIGS. 5 and 6, but showing another embodiment of the variable stop means.

DETAILED DESCRIPTION OF THE PREFERRED EMBODIMENTS

Figure 1:
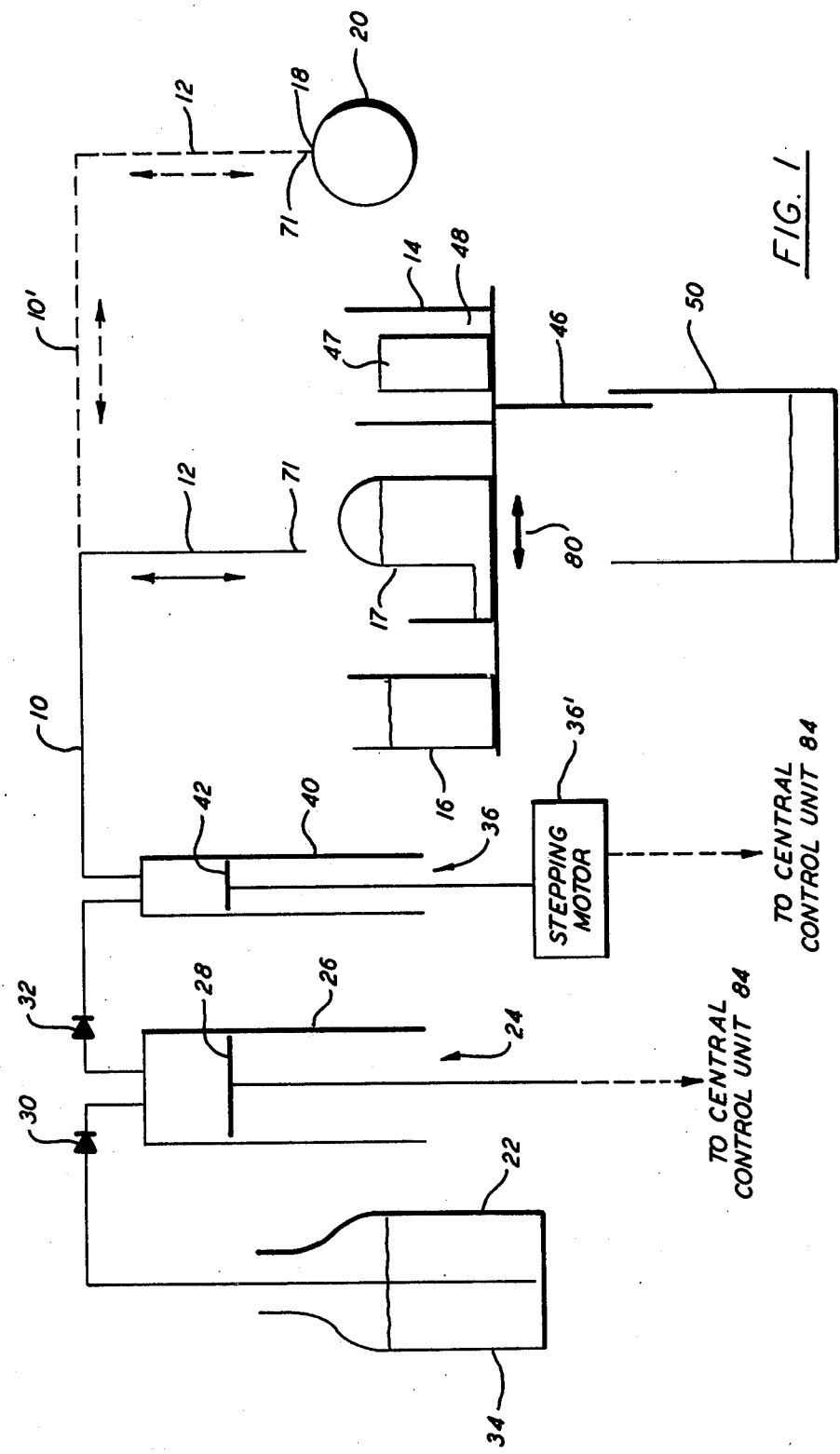
FIG. 1 is a schematic representation of automatic sample preparation apparatus in accordance with the present invention.

Referring to the drawings in detail, there is illustrated apparatus for automated series analysis of sample liquid such as, for example, blood or urine for a specific component, utilizing an analyzer such as, for example, an atomic absorption spectrometer. Initially, the invention will be described in its simplest form, wherein in the first or primary measuring cycle the sample only is analyzed and in the second or secondary measuring cycle the sample plus a liquid additive is analyzed. In this example the sample is independent of the amount of solvent contained therein, as in a graphite tube assembly the solvent evaporates prior to the actual measurement. Later in the description, disclosure will be made of installations wherein it is necessary to add solvent to the liquid sample, usually in an amount equal to the amount in the liquid additive.

As best seen in FIG. 1, the apparatus includes a metering probe 10 having an inlet end portion 12 with a capillary tip 71 which, in operation, is periodically dipped into vessels 14, 16 and 17 and moved to a sample introduction means 18 of an atomic absorption spectrometer 20. Vessel 14 is a container for rinse fluid and vessel 16 is a container for the sample being analyzed, while vessel 17 is a container for liquid additive. As indicated by arrow 80 in FIG. 1, the container arrangement is mounted for movement in such a manner as to bring one container at a time underneath the intake end 12 of the metering probe 10, as will be discussed more fully hereinafter. It is noted that the rinse fluid container 14 is provided with a drain line 46 that leads to a collector vessel 50. The end opposite the inlet 12 of the metering probe is connected to a pump system, which includes a stepping motor driven rinse fluid pump 24, having an inlet connected to a rinse fluid reservoir 22 by a line containing a check valve 30. The discharge of this pump is connected to a second pump 36 via a line containing a check valve 32 so that the rinse fluid delivered by pump 24 is unidirectional. The second pump 36 is driven by a stepping motor 36' controlled by central control unit 84 in such a manner that rinse fluid may be delivered through the metering probe toward the intake end 12. However, during the intake stroke thereof, fluid may be withdrawn from either container 16 or container 17. In addition, during a brief intake stroke following each intake of liquid, a small volumn of air is drawn into the inlet end 12 of the metering probe.

Figure 2:
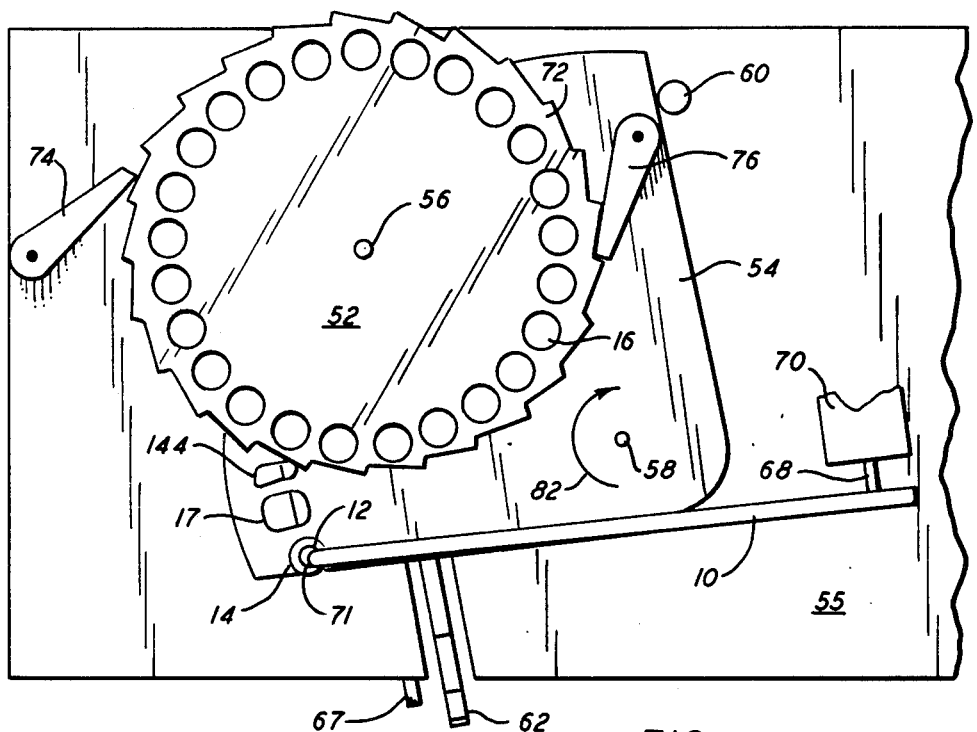
FIG. 2 is a fragmentary elevational view of the apparatus in one operational position.
Figure 3:
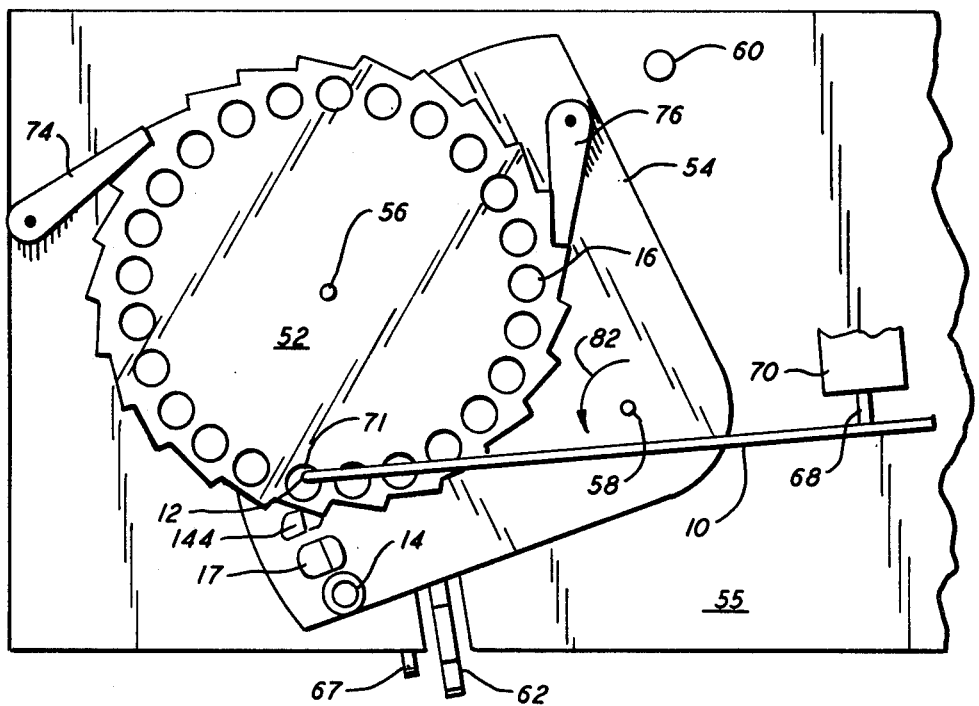
FIG. 3 is a fragmentary elevational view similar to FIG. 2, but showing the apparatus in another operational position.
Figure 4:
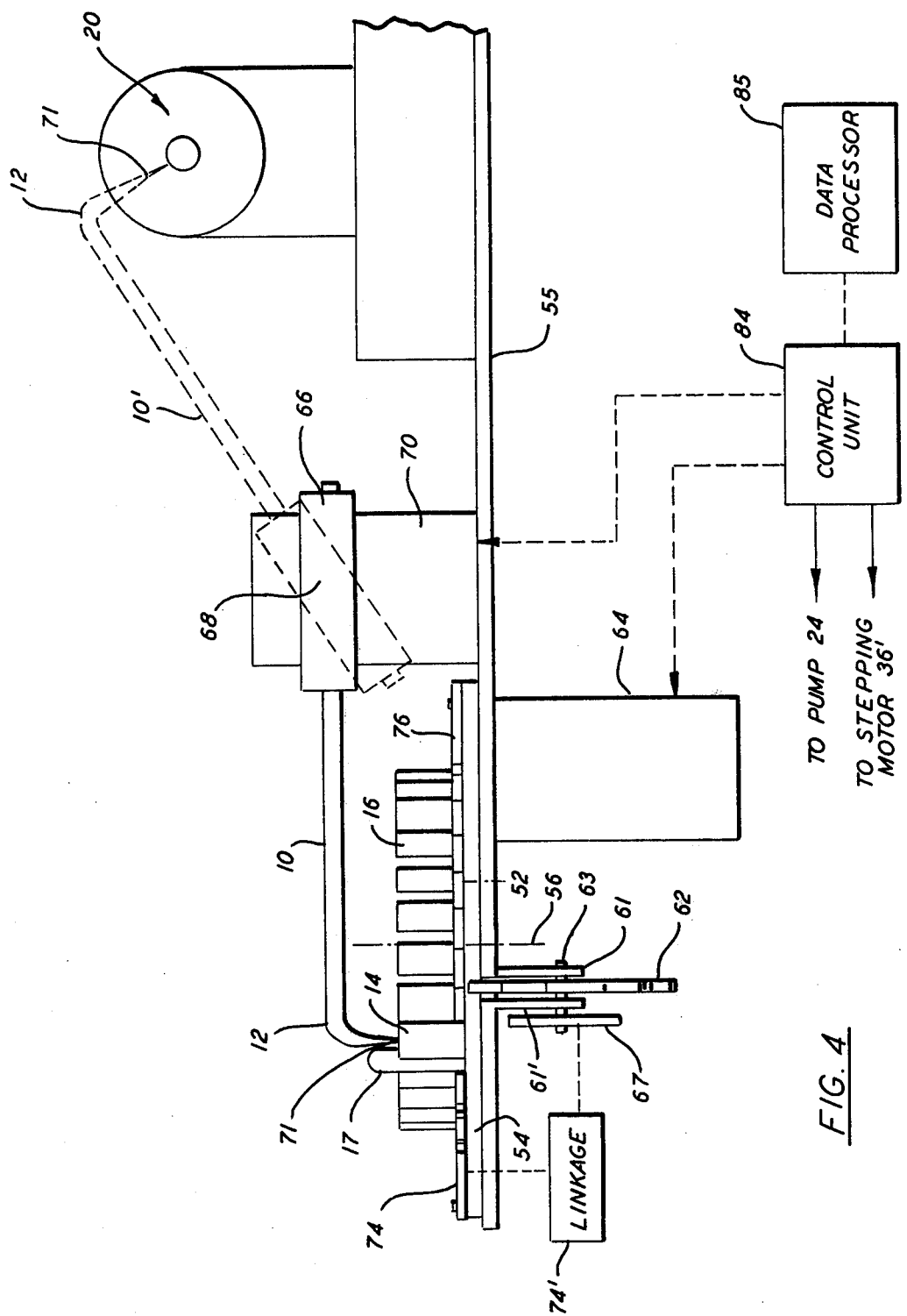
FIG. 4 is a side elevation of the apparatus of FIG. 2.

As best seen in FIGS. 2 to 4, the metering probe 10 is supported by a suitable mounting 66 which permits rotation of the probe about a vertical axis. The mounting member 66 is, in turn, mounted for rotation between two extreme positions by an adjusting or servo motor 70 about an axis 68, perpendicular to the vertical axis. Servo motor 70 is controlled by the central control unit 84. FIG. 4 shows the metering probe 10 in solid line in a first extreme position in which the capillary tip 71 is in the rinse fluid container 14, and in a second extreme position indicated by a broken line 10' wherein the capillary tip 71 is in the sample introduction opening 18 of the graphite tube assembly 20 of the atomic absorption spectrometer.

As best seen in FIGS. 2 and 3, the apparatus employs a carousel-type sample platter consisting of a turntable 52 mounted on a base plate 54 for rotation about a vertical axis 56. The turntable carries a ring of sample containers 16 concentric with its axis of rotation. The base plate 54 is eccentrically pivotable, as indicated by arrow 82, about an axis 58 between a fixed stop member 60 and a variable stop means, by a motor 64 (FIG. 4) controlled by the central control unit 84. The variable stop means is illustrated in the form of a ratchet wheel 62 mounted on a shaft 63, which is supported by brackets 61 and 61' depending from the main frame or supporting structure 55 beneath the base plate 54. The ratchet wheel 62 coacts with a pawl 65 mounted towards the periphery of the base plate 54. In the embodiment illustrated in FIGS. 5 and 6, ratchet wheel 62 has stop faces 64 and 64', which are separated from each other by teeth 66 and 66'. These elements are so arranged that when the base plate 54 is pivoted anticlockwise (as viewed in FIGS. 2 and 3) toward the ratchet wheel 62, the pawl 65 engages one of the teeth 66 or 66' to thereby rotate the ratchet wheel 62 clockwise about its axis 63 until the successive, respective, stop face 64 or 64' engages the bottom side of the base plate 54. FIG. 5 shows the base plate 54 in engagement with the stop face 64, after the pawl 65 has acted upon the tooth 66, corresponding to the pivotal movement of the base plate about its axis 58 through a large angle. At this time the base plate is in its position, as shown in FIG. 3.

FIG. 6 shows the base plate 54 in engagement with the stop face 64', after the pawl 65 has acted upon the tooth 66', corresponding to the pivotal movement of the base plate about its axis 58 through a small angle. When the ratchet wheel is in its position as shown in FIG. 6, the base plate 54 is in a position intermediate those shown in FIGS. 2 and 3, whereby the capillary tip 71 of the probe 10 can be dipped into the liquid additive container 17.

As best seen in FIGS. 2 and 3, the base plate 54, in addition to carrying the rotatable table 52, also carries the rinse fluid container 14 and the liquid additive container 17. These containers are so positioned that the liquid additive container is interposed between the rinse fluid container and the rotatable table 52. When the base plate 54 is in engagement with the fixed stop member 60, as shown in FIG. 2, the rinse fluid container 14 is positioned underneath the capillary tip 71 of the probe 10 so that the tip may be dipped into the container 14 by pivoting the probe 10 about its horizontal axis. When the base plate is positioned as shown in FIG. 3, it is in engagement with the stop face 64 of the ratchet wheel 62. This corresponds to the positional relationship shown in FIG. 5 and, at this time, the capillary tip 71 of the probe 10 is positioned above one sample container 16 so that the tip may be dipped into the container by pivoting the probe about its horizontal axis.

Still referring to FIGS. 2 and 3, the rotatable table 52 is provided with teeth or serrations 72 about its periphery, which are adapted to receive a stop latch 76 that interlocks in such a manner as to prevent anticlockwise rotation of the table 52 during the time when the base plate 54 is pivoting clockwise. On the opposite side of the table 52 there is provided a second stop latch 74, which is mounted for engagement with the serrations 72. This stop latch is controlled by linkage 74' that engages a cam wheel 67 mounted on the shaft 63 (FIG. 4). The control curve on the cam wheel 67 is formed so that the stop latch 74 engages a serration 72 on the table only after both measuring cycles, corresponding to each sample, have been completed. As a result, upon the completion of both measuring cycles, when the base plate 54 pivots towards the variable stop, the rotatable table 52 is advanced one step to place the next succeeding sample in operative position.

Reverting to FIG. 1, the rinse fluid vessel 14 is designed as an overflow type vessel, having an inner chamber 47 and an outer annular chamber 48, with a drain duct 46 leading to a collector vessel 50 for the used rinse fluid. The dimensions of the inner chamber 47 are so selected that when the capillary tip 71 of the probe is dipped therein, and at full stroke of the stepping motor pump 24, the inlet end 12 of the metering probe will be completely rinsed with the rinsing fluid. As a result, when the probe is at the rinse station, rinse liquid ejected through the probe tip fills the inner chamber 47 and overflows into the outer chamber 48 from which it flows to the waste container 50. This accomplishes the rinsing of both the interior and exterior of the probe, so that after completion of this operation no significant contamination occurs when the capillary tip is later immersed.

The liquid additive container 17 is in the form of a pneumatic trough-like vessel so that small amounts of liquid additive will always be able to flow from the interior of the container if liquid additive is removed from the withdrawal portion by means of the capillary tip 71 of the probe.

Still referring to FIG. 1, the rinse fluid pump 24 has, for example, a complete stroke of about 2 ml. and the second pump 36 has a stroke of about 50 $\mu$l. The controlled stepping motor 36' is selected so as to have 5000 steps which correspond to one stroke or a volume of about 50 $\mu$l of the pump 36. The number of steps is adjusted by the central control unit 84 in such a way that during a measuring cycle 20 $\mu$l (equal to 2000 steps) of sample liquid will be aspirated, 10 $\mu$l (equal to 1000 steps) of liquid additive will be aspirated, and 5 $\mu$l (equal to 500 steps) of air will be aspirated after each intake of liquid.

Figure 8:
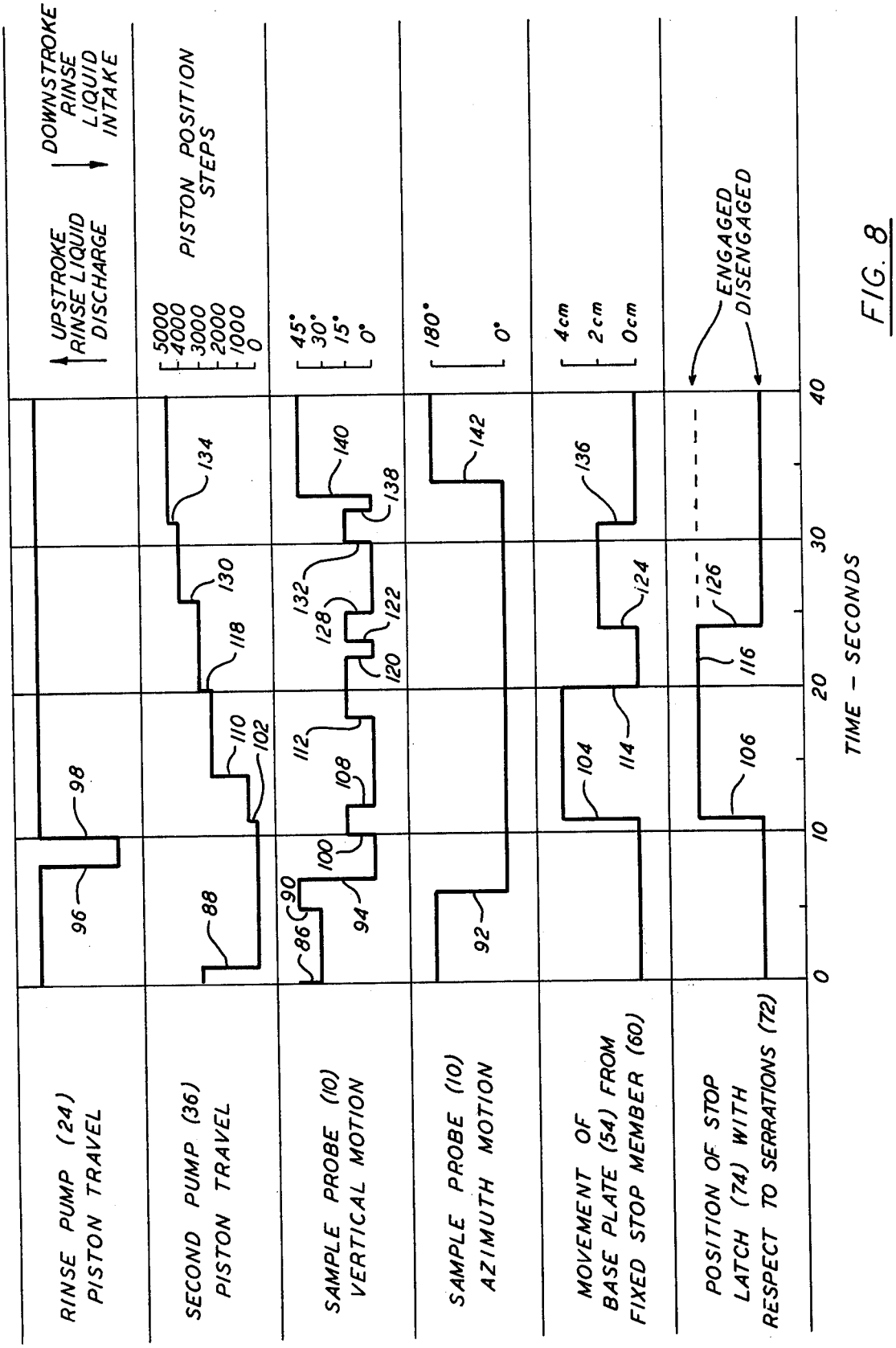
FIG. 8 is a timing diagram showing the time, motion, and functional relation between various entities of the apparatus, which will be referred to in explaining its operation.

It will be appreciated that the control of the pumps 24, 36, the motors 64, 70 and other elements which require synchronized control, is effected by the central control unit 84. The stroke of the rinse fluid pump 24 is preset; the number of steps of the stepping motor 36' for the pump 36 is adjustable at and stored in the central control unit and thus may be called from same by a data processor 85 for evaluation of the measuring signals. In one form the data processor includes a microcomputer in which the control program, including the number of steps of the stepping motor 36', is stored. As pointed out hereinbefore, in the form of the invention presently being described, each complete cycle of operation includes two measuring cycles. In the first measuring cycle, only the sample is analyzed, and in the second measuring cycle the sample plus the liquid additive is analyzed. For simplicity, only the second measuring cycle will be described in detail, because the first measuring cycle is similar thereto, but with the omission of the steps concerning the addition of the liquid additive. Thus, briefly, in the first measuring cycle rinse fluid pump 24 is actuated to fill the entire system including the metering probe with rinse fluid. The capillary tip 71 is dipped into the rinse fluid vessel 14 and rinse fluid is expelled, thereby cleaning the interior and exterior thereof. Thereafter, the capillary tip is dipped into the sample vessel 16, and a partial intake stroke of the pump 36 aspirates a preselected quantity of sample liquid. The capillary tip is then removed from the sample vessel and a further partial intake stroke of the pump 36 aspirates a small preselected quantity of air into the capillary tip. Thereafter, the tip is again dipped into the rinse fluid vessel 14 to decontaminate the exterior thereof before being positioned over the sample introduction opening 18 in the graphite tube assembly of the atomic absorption spectrometer. The timing diagram of FIG. 8 illustrates the correlation of the various elements of the system during the second measuring cycle. Referring in particular to FIG. 8, arbitrarily, the condition of the apparatus at the starting point or time of zero seconds, is assumed to be that point in time at which the capillary tip 71 of the metering probe 10 is positioned above the sample introduction opening 18 of the graphite tube assembly 20. In this position the inlet end 12 of the metering probe 10 is filled with a measured quantity of liquid. After a starting pulse originating from the control device of the atomic absorption spectrometer, the probe 10 is pivoted about its horizontal axis to such a degree that the capillary tip 71 dips into the sample introduction opening 18. This position is shown in FIG. 4 by the broken lines 10' and in FIG. 8 it is indicated at 86 by the initial slight return pivot of the metering probe 10. One second thereafter the stepping motor 36' is actuated 3000 steps to move the pump 36 in the direction of delivery to thereby expell 20 $\mu$l of sample and 10 $\mu$l of air (indicated at 88, FIG. 8). In this manner a measured quantity of liquid is transferred to the atomic absorption spectrometer for analysis.

Five seconds after the liquid has been delivered to the atomic absorption spectrometer, the metering probe 10 is pivoted back from the sample introduction opening 18 (indicated at 90, FIG. 8) and moved azimuthally (at 92) until the capillary tip 71 is positioned above the base plate 54 where the probe 10 is pivoted (at 94) to its lowest horizontal position to dip the capillary tip 71 into the inner chamber 47 of the rinse fluid container 14. At this point in time the entire apparatus is in its position as shown in FIG. 2. Thence, the rinse fluid pump 24 is actuated in the direction of discharge (at 96), whereby about 2 ml. of rinse fluid is delivered through the capillary tip 71 into the inner chamber 47 and overflows therefrom to thereby fill the capillary tip and inner chamber 47 with pure fresh rinse fluid. Then, the rinse fluid pump 24 takes a brief intake stroke (at 98), with the check valve 32 in its closed position. During this interval of time, as indicated in FIG. 8 at 100, the metering probe pivots slightly about its horizontal axis 68 so that the capillary tip 71 is relocated above the rinse fluid container 14. It will be appreciated that at this particular point in time the entire metering probe as well as the pumps 24 and 36 are filled with rinse fluid.

Next, in the sequence of operation, the stepping motor 36' takes 500 steps to effect a partial intake stroke of the pump 36 to aspirate 5 $\mu$l of air into the capillary tip 71, as indicated at 102 in FIG. 8. Simultaneously therewith the drive motor 64 is energized so that the base plate 54 pivots anticlockwise about axis 58, i.e., away from the fixed stop member 60 (at 104, FIG. 8). The ratchet pawl 65 at the periphery of the base plate 54 engages a tooth 66 of the ratchet wheel 62 to rotate same until a face 64 abuts the bottom side of the base plate. At this time the base plate is at its position as illustrated in FIG. 3, wherein the capillary tip 71 is again located above a sample container 16 mounted on the rotatable table 52. Because the shaft 63 rotates with the ratchet wheel 62, the cam 67 will also rotate to bring the pawl 74 into engagement with a serration 72 on the rotatable table 52 at the end of said movement, but without advancing the table at this time, as indicated at 106 in FIG. 8.

After about 12 seconds, total elapsed time, the metering probe is again pivoted by the adjusting motor 70 to its lowest horizontal position, as indicated at 108 in FIG. 8, wherein the capillary tip 71 is immersed in sample container 16. Thereafter, the stepping motor 36' drives the pump 36 to aspirate 20 $\mu$l. of sample liquid into the capillary tip 71, as indicated at 110 in in FIG. 8. Then, the capillary tip is lifted from the sample container by energizing the adjusting motor 70, as indicated at 112, and the base plate 54 is again returned to its engaged position with the fixed stop member 60, by means of the drive motor 64, as indicated at 114, while the stop latch or pawl 74 remains in engagement with the serration 75, as indicated at 116. During this movement of the base plate, the stepping motor 36' drives the pump 36 to aspirate 5 $\mu$l of air into the capillary tip 71, as indicated at 118. After the base plate 54 has reached its final position at the fixed stop member 60, the adjusting motor 70 is briefly energized to immerse (at 120) and withdraw (at 122) the capillary tip 71 in the inner chamber 47, which is filled with rinse fluid at this time. As a result the capillary tip is decontaminated and any sample material adhering to the exterior thereof is removed. At this stage of the operation, about 22 seconds have elapsed from the start of the measuring cycle being described.

Next, in the sequence of operations, the base plate 54 is again pivoted (indicated at 124, FIG. 8) in an anticlockwise direction by the energization of the drive motor 64 so that the pawl 65 mounted on the base plate 54 acts on the tooth 66' of the ratchet wheel 62 to rotate same, with its shaft 63, until the bottom side of the base plate 54 engages the stop face 64' (FIG. 6). During this time the stop latch or pawl 74 is maintained in engagement with the serration 72 by the cam wheel 67 and its associated linkage 74', so that, with the anticlockwise rotation of the base plate 54, the rotatable table 52 is advanced in a clockwise direction. At the termination of the movement of the base plate 54, when its bottom side abuts the stop face 64' of the ratchet wheel 62 (FIG. 6), the rotatable table will have been advanced one step to thereby position the next subsequent sample container 16 in its operative position. Also, at the termination of this movement, the cam wheel 67, which rotates together with the ratchet wheel 62, has been rotated so that the pawl 74 is disengaged from the serration 72 on the rotatable table 62, as indicated at 126 in FIG. 8. The capillary tip 71 is at this time located above the liquid additive container 17 so that pivotal movement (at 128) of the metering probe to its lowest horizontal position by means of the adjusting motor 70 dips the tip into the withdrawal portion of the liquid additive container 17. At this point in time 25 seconds have elapsed from the initiation of the cycle being described.

As a next step, the stepping motor 36' is again actuated to effect a partial intake stroke of the pump 36 so that the capillary tip 71 aspirates 10 μl. of liquid additive, as indicated at 130 in FIG. 8. Subsequently, the adjusting motor 70 is actuated and the capillary tip is lifted from the container 17 (at 132).

After a further partial intake stroke of the pump 36 for aspirating 5 μl. of air into the capillary tip (134, FIG. 8), the base plate 54 is moved to its position (136) wherein it is in engagement with the fixed stop member 60 by means of the drive motor 64. At this instant of time the capillary tip 71 is back again in the position as shown in FIG. 2 and, in the same manner as before, the adjusting motor 70 is briefly energized to immerse (138) the tip in the inner chamber 47, which is filled with rinse fluid to decontaminate it by removing any liquid additive adhering to the exterior thereof.

After immersion in the rinse fluid container 14, the metering probe 10 is pivoted by means of the adjusting motor 70 to its opposite end position (140, FIG. 8), while simultaneously it is pivoted azimuthally (142) until the capillary tip 71 is positioned above the sample introduction opening 18 in the graphite tube assembly 20 of the atomic absorption spectrometer. This completes the timing diagram of FIG. 8. At this point in time the system is in position for pivoting the probe 10 about is horizontal axis to dip the capillary tip 71 into the sample introduction opening 18 and introduce a measured quantity of liquid sample, liquid additive and air into the atomic absorption spectrometer for analysis, thereby completing the second measuring cycle, as well as completing the complete cycle of operation. The apparatus is now ready to commence the first measuring cycle of a new complete cycle of operation.

In the foregoing example, the invention was described in its simplest form, wherein the first measuring signal of the sample, only, was obtained in the first measuring cycle, and the second measuring signal was obtained of the sample after the addition of 10 μl. of liquid additive in the second measuring cycle. The sample liquid may, for instance, be urine of which the quantity of lead contained therein is to be determined, and the liquid additive is lead nitrate in water ($C_A = 250$ mg/l).

In the case described above, the quantity of the component to be determined in the sample is determined according to the general relation $$M_P = S_1 \times e$$

from the signal measured $S_1$ obtained for the sample, only, in the first measuring cycle; e represents a calibration factor for the particular sample liquid. Generally, this calibration factor is:

$$e = \frac{M_m - M_n}{S_m - S_n}$$

wherein $M_m$ and $M_n$ are the amounts of the component in question yielding measured signals $S_m$ and $S_n$. In the present specific case $M_m = M_P + M_A$, i.e. it is the sum of the amount of $M_P$ of the component to be determined in the sample P and of the amount of $M_A$ added with the liquid additive A, and $M_n = M_P$. Then, $S_2$ is the signal measured in the secondary measuring cycle.

This results in:

$$M_P = \frac{S_1}{S_2 - S_1} M_A$$

for evaluation of the measured signals $S_1$ and $S_2$ as obtained from one sample of liquid; with $M_P = C_P \times V_P$ and $M_A = C_A \times v_a$ the respectively selected units of concentration are (mg. per l.):

$$C_P = \frac{S_1}{S_2 - S_1} \cdot C_A \cdot \frac{V_A}{V_P}$$

This formula is preprogrammed in the data processor 85, wherein $C_A$ is a constant, and $V_A$ and $V_P$, respectively, are the number of steps of the stepping motor 36', which are either stored in or may be called-up from the central control unit.

The apparatus as described above may be readily adapted to a measuring method in which the addition of the liquid additive will afffect the measuring signal. In that case a solvent container 144, FIGS. 2 and 3, will be mounted on the base plate 54 in addition to the raise fluid container 14 and liquid additive container 17 which, like the liquid additive container 17, is designed as a pneumatic trough. The container 144 contains the same pure solvent as employed in the liquid additive. The measured signal $S_1$ in the first measuring cycle will then not be taken of the measuring sample P alone, but of a sample to which there has been added a volume of solvent identical to the volume $V_A$ of the liquid additive added in the secondary measuring cycle. In this embodiment, the ratchet wheel 62, as seen in FIG. 7, includes an additional stop face 64" and an additional tooth 66", which are designed to position the base plate 54 so that the solvent container 144 is below the metering probe 10 during an appropriate portion of the first measuring cycle. The cam wheel 67, mounted on the shaft 63 together with the ratchet wheel 62, is designed so that the rotatable table 52 will advance only with the second anticlockwise pivotal movement of the base plate during the secondary measuring cycle.

The time sequence of operation is programmed in a manner similar to that described hereinbefore, and the number of steps of the stepping motor 36' is adjusted by the central control unit or stored in the microcomputer. Evaluation of the measuring signals is, as follows:

$$C_P = \frac{S_1}{S_2 - S_1} \cdot C_A \cdot \frac{V_A}{V_P + V_L}$$

with $V_L = V_A$.

The apparatus, for use in combination with an atomic absorption spectrometer, has been described, wherein the signal measured is determined by the respective quantitities of sample. However, this apparatus may readily be employed in combination with an optical absorption system, wherein the signal measured is dependent on the concentration of the component to be determined. In the simplest case, the procedure follows the modification last discussed hereinbefore, with the extinctions being measured, respectively; the evaluation formula being as follows:

$$C_P = \frac{E_1}{E_2 - E_1} \cdot C_A \cdot \frac{V_A}{V_P + V_L}$$

For convenience, $V_A$ and $V_P$ and $V_L$ are selected to be equal, so that:

$$C_P = \frac{E_1}{E_2 - E_1} \cdot \frac{C_A}{2}$$

In measuring methods off this kind, the general formula for the calibration factor is:

$$e = \frac{\frac{C_P V_P + C_m V_m}{V_P + V_m} - \frac{C_P V_P + C_n V_n}{V_P + V_n}}{S_m - S_n}$$

It will be appreciated that the apparatus may be further modified by making corresponding changes in the time sequence program, by making corresponding changes in the design of the ratchet wheel 62 and the cam member 67 and by making corresponding changes in the evaluation formula in such a way as to perform a number of calibrating measurements with one sample in either a quantity dependent or a concentration dependent measuring method. When employing such a method, the ratchet wheel 62 and the cam wheel 67 coact in such a way as to advance the rotatable table only after the last measuring cycle has been performed with one particular liquid sample.

Thus, an improved automatic sample preparation apparatus and method for making successive measurements with an analyzer has been shown. Although specific embodiments have been illustrated and described, it will be obvious to those skilled in the art that various modifications may be made without departing from the spirit of the invention, which is intended to be limited solely by the appended claims.

What is claimed is:

1. A method for making successive measurements with an analyzer comprising, for each complete cycle of operation, in controlled sequence, the steps of:
   picking up with a single stepwise movable metering probe, in a first measuring cycle, a sample for measurement from a sample container and a small volume of air;
   introducing said sample and the small volume of air into the inlet of said analyzer;
   picking up with said metering probe, in a secondary measuring cycle, a sample for measurement from said sample container and a small volume of air, and picking up with said metering probe a metered quantity of liquid additive and a second small volume of air;
   introducing said sample, said liquid additive and said air picked up in said secondary measuring cycle into the inlet of said analyzer.

2. A method according to claim 1 wherein there are a plurality of secondary measuring cycles in which different, respective, liquid additives are picked up by said metering probe and introduced into the inlet of said analyzer.

3. A method according to claim 2 wherein different preselected quantities of the same liquid additive are picked up in the secondary measuring cycles, respectively.

4. A method according to claim 2 wherein the liquid additive in each secondary measuring cycle contains a predetermined concentration of a solvent of the component to be determined in the sample.

5. A method according to claim 3 wherein the liquid additive in each secondary measuring cycle contains a predetermined concentration of a solvent of the component to be determined in the sample.

6. A method according to claim 1 wherein a metered quantity of pure solvent is also picked up in the first measuring cycle.

7. A method according to claim 4 wherein the amount of liquid solvent picked up is equal to the amount of liquid additive picked up.

8. A method according to claim 3 wherein, in each of said plurality of secondary measuring cycles, respectively, different amounts of solvent, equal to the respective amounts of liquid additive, are picked up.

9. A method according to claim 1 further including the step of externally rinsing said metering probe before each intake of liquid and before introduction to the inlet of said analyzer.

10. A method according to claim 9 further including the step of externally and internally rinsing said metering probe between each complete cycle of operation.

11. Automatic sample preparation apparatus for making successive measurements with an analyzer comprising, in combination;
    a base plate;
    a rotatable table for receiving a plurality of sample containers mounted for rotation on said base plate, means for controlling the advance of said table in a stepwise manner in accordance with the number of measuring cycles in a complete cycle of operation;
    a rinse fluid container mounted on said base plate;
    a liquid additive container mounted on said base plate adjacent said rinse fluid container;

means mounting said base plate for pivotal movement between a fixed stop member and a variable stop means, respectively;

a metering probe having a capillary tip, means mounting said probe for pivotal movement about two mutually normal axes to dip said tip into said containers one at a time and into an inlet of said analyzer;

pumping means including a stepping motor for passing rinse fluid through said metering probe to said rinse container and for picking up metered quantities of liquid in said capillary tip from said sample containers and from said liquid additive container for delivery to said inlet of the analyzer; and central control means for coordinating the movement of said base plate, rotatable table, metering probe and pumping means.

12. Apparatus according to claim 11 wherein said variable stop means includes a rotatable ratchet wheel having a plurality of alternately disposed teeth and stop faces, and a pawl linked to said base plate for coacting with said ratchet wheel, thereby to provide variable stop positions for said base plate.

13. Apparatus according to claim 12 wherein the number of stop faces on said ratchet wheel is equal to the number of pivoting movements of the base plate in one measuring cycle.

14. Apparatus according to claim 13 wherein the shape of the teeth and the angular distance between the stop faces of the ratchet wheel determine the pivoting angle of the base plate.

15. Apparatus according to claim 11 wherein said means for controlling the advance of the rotatable table in a stepwise manner and said variable stop means are coupled together.

16. Apparatus according to claim 12 wherein said means for controlling the advance of the rotatable table in a stepwise manner includes a cam member rotatable with said ratchet wheel, a stop latch engageable with said rotatable table for preventing movement thereof, and linkage means interconnecting said cam member and said stop latch, whereby the cam controls the position of the stop latch with respect to the rotatable table.

17. Apparatus according to claim 11 wherein said pumping means includes a first rinse fluid pump adapted to deliver rinse fluid in a single direction, a second pump driven by a stepping motor connected in series with said first pump, the outlet of said second pump being connected to said metering probe in fluid flow communication.

18. Apparatus according to claim 11 wherein said central control means includes a central control unit for preprogramming the time sequence of the operational steps of the apparatus, and for adjusting the number of steps of the stepping motor.

19. Apparatus according to claim 11 wherein said central control means includes a data processor for evaluation of the signals measured.

20. Apparatus according to claim 19 wherein said data processor is a mircrocomputer integral with the apparatus.

21. Apparatus according to claim 20 wherein the time sequence control and the number of steps of the stepping motor are stored in the microcomputer.

22. Apparatus according to claim 11 wherein said liquid additive container is in the form of a pneumatic trough.

23. Apparatus according to claim 17 wherein said rinse fluid container is in the form of an overflow vessel and the capacity of the overflow vessel is smaller than the liquid volume delivered by one stroke of the first rinse fluid pump.

* * * * *